United States Patent [19]
Baylink et al.

[11] Patent Number: 5,599,679
[45] Date of Patent: Feb. 4, 1997

[54] AMINO PROCOLLAGEN 1(I) PEPTIDES

[76] Inventors: David J. Baylink, 1428 Serpentine Dr., Redlands, Calif. 92373; Susan Linkhart, 220 Gabrielle Way, Redlands, Calif. 92374

[21] Appl. No.: 479,233

[22] Filed: Jun. 7, 1995

Related U.S. Application Data

[63] Continuation of Ser. No. 829,142, Jan. 31, 1992, abandoned.
[51] Int. Cl.$^6$ ............................ G01N 33/53; C07K 14/78
[52] U.S. Cl. .................. 435/7.9; 530/324; 530/387.9; 530/325; 530/326; 530/327; 530/328; 530/329
[58] Field of Search ........................... 435/7.1, 7.9, 7.92; 530/327, 328, 329, 388.85, 389.1, 387.9, 324, 325, 326

[56] References Cited

FOREIGN PATENT DOCUMENTS 2208865  4/1989  United Kingdom ............. C07K 3/28

OTHER PUBLICATIONS

Davis et al., "Development of a serum assay for procollagen type I aminopropeptitde," Gastroenterology 88 (5 pt 2): 1655. (May 1985).

Davis et al., "An Immunohistochemical and Serum ELISA study of type I and type III Procollagen Aminopeptides in Primary Biliary Cirrhosis," Am. J. of Pathology, 128(2):265–275 (Aug. 1987).

Simon et al, "Serum Levels of Type I and III Procollagen Fragments in Paget's Disease of the Bone," 58(1):110–120. (Jan. 1984).

Foellmer et al., "A Monoclonal Antibody Specific for the Amino Terminal Cleavage Site of Procollagen Type I," Eur. J. Biochem. 134:183–189 (1983).

Chu et al., "Human Proα1 (I) collagen gene structure reveals evolutionary conservation of a pattern of introns and exons," Nature 310:337–340. (Jul. 1984).

Fessler et al., "Biosynthesis of Procollagen", Ann. Rev. Biochem. 47:129–162. (1978).

Fisher et al., "The $M_r$ 24,000 Phosphoprotein from Developing Bone is the $NH_2$–terminal Propeptide of the α1 Chain of Type I Collagen," J. Biol. Chem. 262:13457–13463 (Oct., 1987).

Linkhart et al., "Synthetic Peptide–Based Immunoassay for Amino–Terminal Propeptide of Type I Procollagen; Application for Evaluation of Bone Formation," Clin. Chem., 39:2254–2258 (1993).

Carey et al. "Radioimmunoassay for Type I Procollagen in Growth Hormone–deficient Children Before and During Treatment with Growth Hormone", Pediatric Res. 19:8–11 (1985).

Goldberg et al., "The Carboxyl Fragment Released by Bacterial Collagenase from Human Type I Procollagen: Antibodies to the Propeptide Determinants", Collagen Rel. Res. 5:393–404 (1985).

Melkko et al., "Radioimmunoassay of the Carboxyterminal Propeptide of Human I Procollagen", Clinical Chem. 36:1328–1332 (1990).

Fouser et al., "Feedback Regulation of Collagen Gene Expression: A Trojan Horse Approach", Proc. Natl. Acad. Sci. USA 88:10158–10162 (Nov., 1991).

Ebeling et al. "Utility of Type I Procollagen Propeptide Assays for Assessing Abnormalities in Metabolic Bone Diseases," J. Bone & Min. Res. 7:1243–1250 (Nov. 11, 1992).

*Primary Examiner*—James S. Ketter
*Attorney, Agent, or Firm*—Popovich & Wiles, P.A.

[57] ABSTRACT

Peptides which contain epitopes that mimic epitopes of the amino terminal propeptide of α1 Type I collagen, and antibodies which bind the epitopes, are useful in monitoring bone formation. Assays which employ the peptides and antibodies thereto are particularly useful in diagnosing and monitoring bone related disorders, such as osteoporosis and Paget's disease, among others.

22 Claims, 2 Drawing Sheets

AMINO PROCOLLAGEN 1(I) PEPTIDES

This is a Continuation of application Ser. No. 07/829,142, filed Jan. 31, 1992, now abandoned.

FIELD OF THE INVENTION

This invention relates to methods for determining bone formation rates by measuring levels of the amino terminal propeptide of procollagen alpha (α)1 chain of Type I collagen.

BACKGROUND OF THE INVENTION

Bone formation in vertebrates is a dynamic process involving continuous production of bone and continuous bone resorption. Osteopenia is a general term used to describe any bone-wasting disease in which the rate of bone resorption is greater than the rate of bone formation. Osteoporosis results from a progressive net loss of skeletal bone mass due to an increase in bone resorption exceeding bone formation. Osteoporosis afflicts nearly 20 million people in the United States alone, and total costs from osteoporosis-related injuries amount to at least $7 billion annually (Barnes, *Science* 236:914 (1987)). A major difficulty in monitoring the disease is the lack of a specific assay to measure acute changes which may occur from various treatment regimens. There is a need to have an easy, reliable test for bone formation.

Type I Collagen is unique to connective tissues and is a major component in bone, among other tissues. The normal synthesis and breakdown of this collagen type can be altered during the pathogenesis of many kinds of disease, including osteoporosis. Because bone is a metabolically active tissue throughout life, indicators of Type I collagen turnover could be useful as a markers in metabolic bone disease. However, the major means for estimating the metabolic rate of bone collagen has been to quantify the urinary excretion of hydroxyproline, which is derived from collagenous proteins. This test has proven tedious, associated with several sources of error, and not specific for Type I collagen. Azria, *Calcif. Tissue Int.* 45:7–11 (989).

Each Type I collagen fiber is composed of three long, helical polypeptide chains (α chains) that bind tightly to each other. Each Type I collagen polypeptide is synthesized as a larger procollagen molecule, containing additional sequences at both the amino and carboxy termini. It appears that the large amino and carboxy terminal ends of the procollagen are important in the alignment and binding of the trimer. The amino and carboxy terminal propeptides are cleaved extracellularly by specific proteinases before the α chains are assembled into fibers.

The portion of the procollagen polypeptide removed from the carboxy terminus, referred to as the carboxyterminal propeptide of Type I collagen, has been found in blood, where its concentration changes during growth and in metabolic bone disorders. Radioimmunoassays for the carboxyterminal propeptide have been reported (e.g., Taubman et al., *Science* 186:1115–1117 (1974); Taubman et al., *Proc. Soc. Exp. Biol. Med.* 152:284–287 (1976); and Parfitt et al. *J. Bone Min. Res.* 2:427–436 (1987)), including the use of digests of carboxy terminal procollagen obtained from cultured human skin fibroblasts and then purified by digestion, lectin affinity chromatography, gel filtration and ion exchange HPLC (e.g., Meikko et al., *Clin. Chem.* 36:1328–1332 (1990)). These tests, however, are difficult and expensive to prepare and have not found widespread use.

Little work has been reported with the amino terminal propeptide of Type I collagen. In 1987 it was reported that, in a group of patients with primary biliary cirrhosis, both Type I and Type III procollagen aminopropeptides were measured. This was performed by ELISA using purified antigen from calf skin. This study found that the amount of Type I amino propeptide was unchanged, regardless of the degree of histologic fibrosis on liver biopsy, whereas Type III procollagen varied significantly with disease state (Davis et al., *Am. J. Path.*, 128:265 (1987)).

Accordingly, there remains a need for a sensitive and specific measure of bone formation which is practical to produce and convenient to use. The digests of native procollagen, for example, are not conveniently prepared, do not allow for the production of antibodies to well-defined epitopes of interest, and are expensive to develop. The present invention circumvents many of these problems while meeting the requirements for sensitivity and specificity, and fulfills other related needs.

SUMMARY OF THE INVENTION

Compositions and methods are provided which are useful in determining the levels of the amino propeptide of human Type I collagen. The level of the amino propeptide is used as a marker of collagen synthesis in an individual, and thus serves as a sensitive and specific indicator of bone formation. Assays for the amino propeptide find a variety of uses, including use in diagnosing metabolic bone disorders, such as osteoporosis or postmenopausal rapid bone losers, monitoring the efficacy of therapeutic regimens designed to treat such disorders, and determining the extent of imbalances between bone formation and resorption; etc.

The assays of the invention employ peptides of the amino terminus of procollagen α1 Type I and antibodies specific to said peptides. More particularly, peptides of the invention contain from six to fifty amino acids and have at least one epitope which immunologically competes with the native amino-terminal propeptide of procollagen α1 Type I. In a preferred embodiment, the epitope(s) is (are) contained in the sequence Gln-Glu-Glu-Gly-Gln-Val-Glu-Gly-Gln-Asp-Glu-Asp ($PEP_{23-34}$ [Seq. ID No. 1]). The peptides will typically further comprise at least one Cys and/or Tyr residue at the N- or C-terminus to facilitate conjugation, for labeling, and the like. Other peptides from the amino terminus of the procollagen molecule are also provided. Antibodies, either polyclonal or monoclonal, are provided which bind specifically to a peptide of the invention and thus allow a variety of immunoassay formats. Particularly preferred are radioimmunoassays and enzyme-linked immunosorbent assays to conveniently determine levels of amino terminal procollagen Type I in a sample, such as serum or plasma, obtained from an individual of interest.

DESCRIPTION OF THE SPECIFIC EMBODIMENTS

Figure 1:
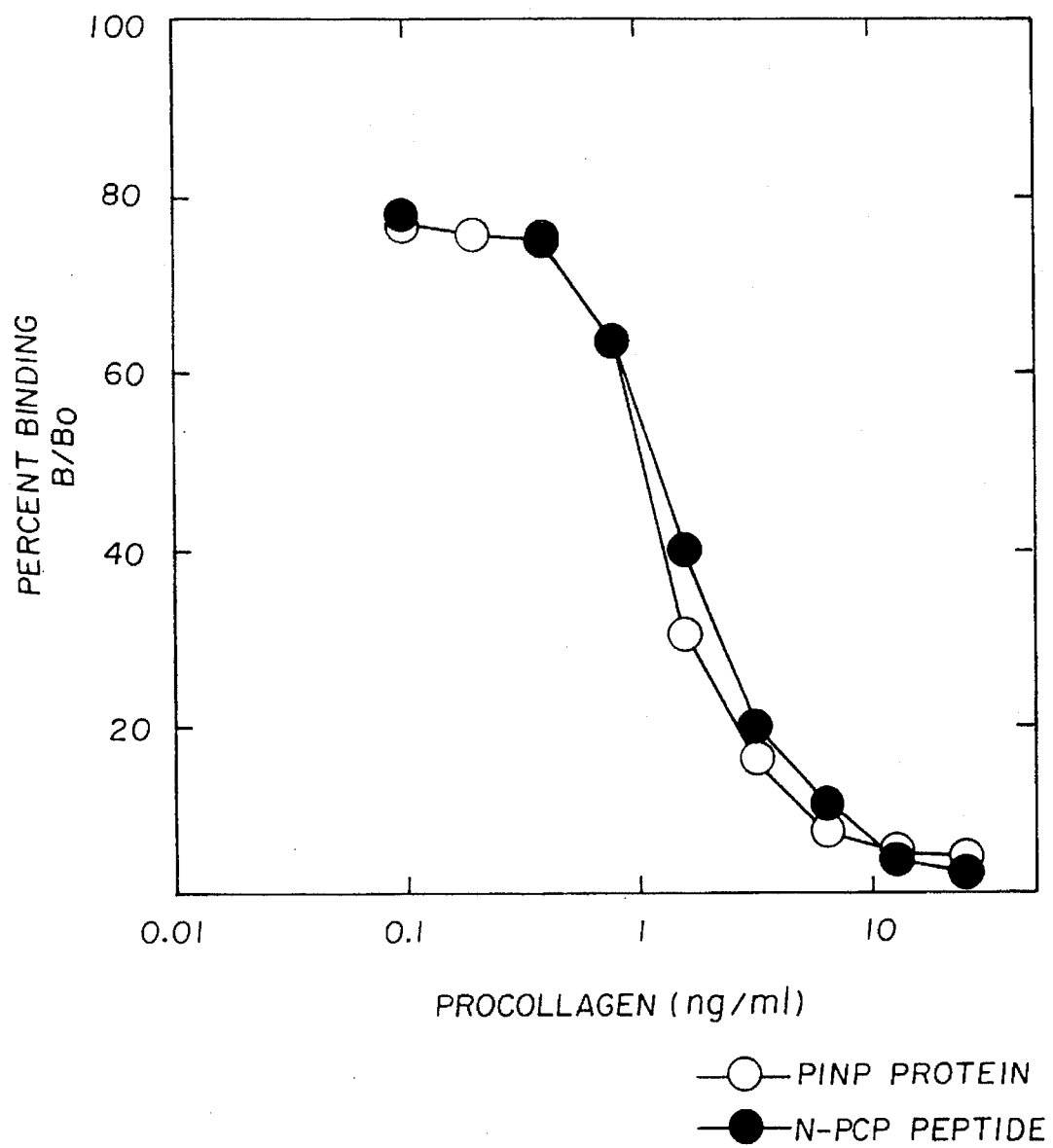
FIG. 1 is a graph of percent binding ($B/B_o$) versus procollagen concentration (ng/ml), which shows antiserum from a rabbit injected with the peptide Seq. ID No. 2, which was diluted and incubated with varying amounts of either the synthetic peptide itself or amino procollagen alpha 1 (I), which was purified from human skin cells in culture. This shows that both the synthetic peptide and the native amino procollagen displace in parallel and with a similar magnitude.

The present invention provides peptides derived from the procollagen alpha (α)1 chain of Type I collagen for use in compositions and methods for the diagnosis, screening and monitoring of bone formation in an individual. The peptides and/or antibodies thereto are useful in assays to determine the level of procollagen α1 (I) activity, and, therefore, provide a specific and sensitive determination of bone production.

In preferred embodiments the peptides of the invention are derived from the amino terminal propeptide region of the procollagen α1 chain of Type I collagen. The amino terminal propeptide extends from residues 23 to 161 of the prowl chain of Type I collagen, (residues 1–22 being the signal sequence), where the numbering is according to Tromp et al., Biochem. J. 254:919–922 (1988), which is incorporated herein by reference. Thus, in accordance with the present invention peptides are provided which contain from six to fifty amino acids of the amino terminal propeptide sequence [Seq. ID No. 11] and which peptides contain at least one epitope that is immunologically competitive with the native amino terminal propeptide. Antibodies produced to the peptides, conveniently synthetically produced peptides, can be used to readily determine those peptides which contain at least one epitope which is immunologically competitive using well known assay methods. Competition will typically be due to specific binding by the epitopes for binding to the antibody but, in some cases, steric hindrance in epitope conformation may also contribute to the competition, as such assays typically measure only the end result regardless of the actual mechanism of competition.

In more preferred embodiments described herein, procollagen peptides (PEP) are derived from the N-terminal regions of amino acid residues 23 to 34 ($PEP_{23-34}$; Seq. ID NO. 1), residues 28 to 36 ($PEP_{28-36}$; Seq. ID NO. 3), residues 46 to 53 ($PEP_{46-53}$; Seq. ID NO. 4), residues 52 to 58 ($PEP_{52-58}$; Seq. ID NO. 5), residues 76 to 82 ($PEP_{76-82}$; Seq. ID NO. 6), residues 84 to 91 ($PEP_{84-91}$; Seq. ID. No. 7), residues 97 to 108 ($PEP_{97-108}$; Seq. ID No. 8), residues 112 to 121 ($PEP_{112-121}$; Seq. ID No. 9), or residues 130 to 137 ($PEP_{130-137}$; Seq. ID No. 10).

By procollagen α1 Type I "peptide" of the present invention is meant a contiguous chain of at least six amino acid sequence residues from the procollagen α1 Type I N-terminal propeptide region, sometimes preferably at least eight or nine, sometimes ten to twelve residues, and usually no more than about fifty residues, more usually fewer than about thirty-five, and preferably fewer than twenty-five amino acid residues derived from a selected procollagen α1 Type I propeptide sequence region as set forth herein. The term peptide is used in the present specification to designate a series of amino acids connected one to the other by peptide bonds between the alpha-amino and carboxy groups of adjacent amino acids The peptides can be prepared "synthetically," as described hereinbelow, or by recombinant DNA technology. The peptide will preferably be substantially free of naturally occurring procollagen α1 Type I proteins and fragments thereof. The peptides can be either in their neutral (uncharged) forms or in forms which are salts, and either free of modifications such as glycosylation, side chain oxidation, or phosphorylation, or containing these modifications, subject to the condition that the modification not destroy the immunoreactivity of the peptide as herein described.

Desirably, the peptide will be as small as possible while still maintaining substantially all of the immunoreactivity of a larger peptide. By immunoreactivity is meant the ability of a peptide of the invention to immunologically compete with the amino terminal propeptide of procollagen α1 Type I, and/or which has the ability, when used as an immunogen, to stimulate the production of antibodies, which are capable of specifically binding to the amino terminal propeptide of procollagen α1 Type I.

A preferred immunoreactive procollagen α1 Type I amino terminal peptide of the invention is derived from the N-terminus region, amino acid residues 23 to 34 ($PEP_{23-34}$). A representative peptide embodiment of this region is the peptide of the following sequence:

$PEP_{23-34}$ [Seq. ID No. 1] Gln-Glu-Glu-Gly-Gln-Val-Glu-Gly-Gln-Asp-Glu-Asp wherein the peptide can be optionally flanked and/or modified at one or both of the N- and C-termini, as desired, by amino acids from the procollagen α1 Type I amino terminal propeptide sequence, amino acids added to facilitate linking, labeling, other N- and C-terminal modifications, linked to carriers, etc., as further described herein. In a particularly preferred embodiment of $PEP_{23-34}$ the C-terminal further includes Tyr-Cys residues for convenient labeling, polymerization via disulfide bonds, adsorption, etc., as desired for a particular application. Thus, one $PEP_{23-34}$ peptide so modified has the sequence Gln-Glu-Glu-Gly-Gln-Val-Glu-Gly-Gln-Asp-Glu-Asp-Tyr-Cys [Seq. ID No. 2] and is described in further detail in the Examples below.

Another procollagen α1 Type I amino-terminal propeptide peptide of the invention comprises at least six contiguous amino acid residues derived from the sequence region of amino acid 28 to 36:

$PEP_{28-36}$ [Seq. ID. No. 3] Glu-Gly-Gln-Asp-Glu-Asp-Ile-pro which optionally includes modifications, including at the N- and/or C-termini, such as additional Tyr and/or Cys residues, as desired.

Yet another procollagen α1 Type I amino-terminal propeptide peptide of the invention comprises at least six contiguous amino acid residues derived from the sequence region of amino acid 46 to 53:

$PEP_{46-53}$ [Seq. ID. No. 4] Arg-Tyr-His-Asp-Arg-Asp-Val-Trp which optionally includes modifications, including at the N- and/or C-termini, such as additional Tyr and/or Cys residues, as desired.

Other peptides derived from the amino-terminal propeptide of procollagen α1 Type I include those from the sequence region of amino acid 52 to 58, which has the following sequence:

$PEP_{52-58}$ [Seq. ID. No. 5] Val-Trp-Lys-Pro-Glu-Pro-Cys which, again, optionally includes modifications such as at the N- and/or C-termini. One exemplary modification includes a Tyr at the C-terminus, but other modifications are contemplated within the present invention, as generally set forth herein.

Additional peptides are derived from the amino acid region 76 to 82 of the amino-terminal propeptide procollagen α1 Type I, which region has the sequence:

PEP$_{76-82}$ [Seq. ID. No. 6] Asp-Glu-Thr-Lys-Asn-Cys-Pro which optionally includes modifications, including at the N- and/or C-termini, such as additional Tyr and/or Cys residues, and more preferably a Tyr at the C-terminus of peptide PEP$_{76-82}$, and/or other modifications as desired for the particular application intended.

The invention also includes peptides from the amino acid region 84–91 of the amino-terminal propeptide procollagen α1 Type I, which region has the sequence:

PEP$_{84-91}$ [Seq. ID. No. 7] Ala-Glu-Val-Pro-Glu-Gly-Glu-Cys and optionally includes modifications, including at the N- and/or C-termini, such as additional Tyr and/or Cys residues, more preferably a Tyr at the C-terminus of peptide PEP$_{84-91}$, for example.

Other peptides are derived from the regions of the amino-terminal propeptide of procollagen α1 Type I from residues 97 to 108, 112 to 121, and 130 to 137, which have the following sequences:

PEP$_{97-108}$ [Seq. ID No. 8] Asp-Gly-Ser-Glu-Ser-Pro-Thr-Asp-Gln-Glu-Thr-Thr

PEP$_{112-121}$ [Seq. ID No. 9] Gly-Pro-Lys-Gly-Asp-Thr-Gly-Pro-Arg-Gly

PEP$_{130-137}$ [Seq. ID No. 10] Gly-Arg-Asp-Gly-Ile-Pro-Gly-Gln which peptides optionally includes modifications, including at the N- and/or C-termini, such as additional Tyr and/or Cys residues, and/or other modifications as desired for the particular application intended.

As mentioned above, additional amino acids can be added to the termini of a peptide to provide for ease of linking peptides one to another, for coupling to a carrier, support or larger peptide, for modifying the physical or chemical properties of the peptide, etc. One or more amino acids such as tyrosine, cysteine, lysine, glutamic or aspartic acid, or the like, can be introduced at the C- or N-terminus of the peptide. In addition, a peptide sequence can differ from the native human amino-terminal propeptide of procollagen α1 Type I sequence by being modified by amino terminal acylation, e.g., acetylation, or thioglycolic acid amidation, carboxy terminal amidation, e.g., ammonia, methylamine, etc. In some instances these modifications may provide sites for linking to a support or other molecule.

It will be understood that the peptides of the present invention or analogs thereof, which have immunoreactivity with the amino-terminal of procollagen α1 Type I, may be modified as necessary to provide other desired attributes, e.g., improved immunoreactivity (such as increased immunocompetition with native protein), while increasing or at least not significantly diminishing the immunoreactivity of the unmodified peptide which is derived from the native procollagen sequence. For instance, the peptides may be subject to various changes, such as insertions, deletions, and substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an immunoreactive procollagen epitope will not differ by more than about 20% from the native procollagen sequence, except where additional amino acids may be added at either terminus for the purpose of modifying the physical or chemical properties of the peptide for, e.g., ease of linking or coupling, and the like.

Having identified different peptides of the invention which are immunoreactive with the procollagen amino-terminal propeptide, in some instances it may be desirable to join two or more peptides in a composition or admixture. The peptides in the composition can be identical or different, and together they should provide equivalent or greater immunoreactivity than the parent peptide(s). For example, using the methods described herein, two or more peptides may define different or overlapping immunoreactive epitopes from different or the same N-terminal procollagen region, which peptides can be combined in a cocktail to provide enhanced immunoreactivity.

The peptides of the invention can be combined via linkage to form polymers. Where the same peptide is linked to itself, thereby forming a homopolymer, a plurality of repeating epitopic units are presented. When the peptides differ, e.g., a cocktail representing different procollagen regions, heteropolymers with repeating units are provided. In addition to covalent linkages, noncovalent linkages capable of forming intermolecular and intrastructural bonds are also contemplated by the present invention.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane- 1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). Of course, it will be understood that linkage should not substantially interfere with the immunoreactivity of either of the linked groups.

In another aspect the peptides of the invention can be combined or coupled with other peptides which present procollagen epitopes, e.g., such as those from the carboxy terminal of the procollagen α1 Type I molecule, some of which are described in European patent publication EP 304,292, incorporated herein by reference.

As mentioned above, amino acid arms may be provided at the C- and/or N-terminus of the peptide or oligopeptide. If present, the arms will usually be at least one amino acid and may be 50 or more amino acids, more often 1 to 10 amino acids, and preferably less than 5 amino acids for ease of synthesis. The arms may serve a variety of purposes, such as spacers, to attach peptides to a carrier, to immobilize peptides to a solid phase, etc. To provide useful functionalities for linking to a carrier or solid phase or to form higher-ordered structures, such as dimers, trimers, or other multimers, amino acids, such as tyrosine, cysteine, aspartic acid, or the like, may be introduced at or provided at the C- and/or N-terminus of the arm or peptide. To enhance epitope presentation and/or radiolabeling, of particular interest is the presence of from 1 to 10 amino acids at the C- and/or N-terminus, more preferably 1 to 5 amino acids, and most preferably about 1 to 3. Particularly preferred embodiments of certain peptides described herein are obtained when 3 amino acids are added as an arm, generally at the N-terminus, with the N-terminal residue of the arm, which is preferably Cys. In exemplary embodiments the spacer residues between the peptide and the terminal functional group are Gly. A terminal Cys residue may also be linked through a disulfide linkage to a dithio- or thiofunctionalized support or a thioether linkage to an activated olefin support.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify immunoreactive peptides having immunodominant epitopes of the amino-terminal propeptide of Type I procollagen, and the like.

Alternatively, recombinant DNA technology may be employed, wherein a nucleotide sequence, which encodes a peptide of interest, is inserted into an expression vector, which is transformed or transfected into an appropriate host cell, which is and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1989); Ausubel et al., eds., *Current Protocols in Molecular Biology*, John Wiley and Sons, Inc., New York (1987), and U.S. Pat. Nos. 4,237,224, 4,273,875, 4,431,739, 4,363,877 and 4,428,941, for example, the disclosures of which are incorporated herein by reference. Thus, fusion proteins, which comprise one or more peptide sequences of the invention can be used to present the determinants of the amino-terminal propeptide of α1 Type I collagen.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides and antibodies of the present invention and compositions thereof find use as diagnostic reagents. For example, a peptide as described herein, and/or antibodies to the peptide, may be used to determine the rate of bone formation in an individual. Diagnostic assays for bone formation, often in conjunction with bone resorption assays, can be used to assess net bone balance in an individual. An increase in bone resorption without an adequate compensatory increase in bone formation may result in osteoporosis or another bone disorder. The amount of free amino-terminal Type I procollagen in a particular individual can be monitored over a period of time and progression or regression of bone formation determined. Samples from an individual can also be compared to relative levels determined from a group of similar patients and the variation therefrom used as a marker of disease progression or regression. Thus, the diagnostic assays provided herein can also be used to assess the responsiveness of an individual to a particular treatment regimen for a bone resorption-related disorder, to modify a treatment protocol, or to establish a prognosis for an affected individual. In addition, the diagnostic assays can be used to predict which individuals will be at substantial risk for developing bone-resorption disorders, such as, e.g., osteoporosis. Also, as skin contributes to the total circulating pool of procollagen peptide, the assays described herein can be used to monitor the condition of burn patients or patients with severe skin lesions.

The antibodies and peptides of the invention also find use in immunocytochemistry, such as to identify osteoblasts or other mesenchymal cells that are producing procollagen, thereby identifying cells which are actively producing collagen to be deposited in the surrounding matrix. Other uses include immunoaffinity purification of procollagen Type I, where immunopurification techniques are generally known in the art and can be adapted for the anti-peptide antibodies described herein to isolate procollagen in substantially pure form, as desired. Patient samples can also be analyzed for the presence of the procollagen Type I amino-terminal using the antibodies prepared against the peptides in Western blot techniques, which are described in U.S. Pat. No. 4,452,901, incorporated herein by reference. The antibodies and peptides of the invention can find use in a wide variety of other assays, e.g., screening of genetic libraries, and the like.

As will be recognized by those skilled in the art, numerous types of immunoassays are available for use in the present invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, New York (1988), each of which is incorporated by reference herein.

The samples to be assayed are derived from an extracellular fluid, cell components or cell products, including, but not limited to, cells and cell culture supernatants, cell extracts, tissue extracts, wound fluids, urine, saliva, blood, plasma, serum, and fractions thereof. As the propeptides of procollagen α1 Type I are believed to be cleaved extracellularly, typically the biological sample will be an extracellular fluid or derived therefrom, although cell surfaces may also be assayed.

The peptide and antibody compositions may be used unlabeled or labeled depending upon their application. By label is intended a molecule which provides, directly or indirectly, a detectable signal. Various labels may be employed, such as radionuclides (e.g., $^{125}$I, $^{131}$I, $^{3}$H, $^{14}$C) enzymes, fluorescers, chemiluminescers, enzyme substrates, cofactors or inhibitors, particles (e.g., magnetic particles), combinations of ligands and receptors (e.g., avidin and biotin), dyes, or the like. In addition, the peptides and antibodies thereto may be modified in a variety of ways for binding to a particular surface, such as a microtiter plate, glass or latex bead, tube, filter, chromatographic surface, nitrocellulose paper, cellulose, silica gel, or the like. The particular manner in which peptides and antibodies may be joined to another compound or solid phase surface finds ample illustration in the literature. See, for example, U.S. Pat. Nos. 4,371,515; 4,487,715; and patents cited therein. As mentioned above, reagents such as p-maleimidobenzoic acid, p-methyldithiobenzoic acid, maleic acid anhydride, succinic acid anhydride, glutaraldehyde, hetero-bifunctional cross-linkers, and the like are commonly used for such purposes.

In one assay format, the amount of amino terminal propeptide of α1 Type I collagen in a biological sample is determined in a competition-type assay by measuring the extent that amino terminal Type I propeptide in the sample competes with a peptide of the invention for binding to antibodies specific for the peptide. Although several competitive assay formats are known, in one fluid phase competition assay, such as radioimmunoassay, antibodies and peptides (labeled or capable of being labeled) are allowed to interact in a buffered system under conditions conducive to immune complex formation. A sample suspected of containing the amino terminal propeptide is then added and the system is generally allowed to reach equilibrium. The immune complexes resulting from the incubation are subsequently recovered and the amount of label determined, being proportional to the amount of labeled peptides of the invention bound to the antibody. Alternatively, the sample can first be incubated with the antibody and, subsequently or simultaneously, incubated with a labeled peptide of the invention.

In a solid phase competition type immunoassay the primary antibody, which is immunologically reactive with an epitope contained within the sequence of one of the peptides of the invention, such as, e.g., PEP$_{23-34}$ [Seq. ID No. 1], where the epitope is immunologically competitive with an epitope of amino terminal propeptide of procollagen α1 Type I, is bound, covalently or noncovalently, to a carrier, typically an insoluble solid phase, such as a microtiter well. The biological sample to be tested is incubated with the antibody under conditions conducive to immune complex formation, and either simultaneously or subsequently contacted with at least one of the labeled peptides of the invention, also under conditions conducive to immune complex formation. Specifically bound label is then detected, and the presence or quantity of the amino terminal propeptide of procollagen α1 Type I in the sample determined. Typically, the amount of labeled peptide which is bound to the antibodies is proportional (inversely) to the amount of amino terminal propeptide in the sample. Separation steps (e.g., either physicochemical or immunological) and wash steps may be necessary to distinguish specific binding over background.

In an ELISA type immunoassay, again a variety of formats are contemplated. In one method, the synthetic peptide of the invention is bound to a solid phase, e.g., microtiter well, by adsorption, cross-linking, etc. A test sample is incubated with the anti-peptide antibodies of the invention, and then the mixture is placed in the peptide-coated well and incubated. Antibody, which is not bound by amino terminal propeptide in the sample, is bound to the peptide on the solid phase. After a separation step, the presence and quantity of bound antibodies can be determined, e.g., using a labeled secondary antibody, such as anti-rabbit IgG, when the primary antibodies are produced as rabbit antisera, and a convenient color substrate.

Kits can also be supplied for use with the recombinant or synthetic amino terminal procollagen Type I peptides of the invention in determining levels of procollagen turnover in an individual. Thus, the subject peptide compositions may be provided, usually in lyophilized form, in a container, either alone or in conjunction with additional reagents, such as procollagen-specific antibodies, labels, and/or anti-antibodies, and the like. The peptides and antibodies, which may be conjugated to a label, or unconjugated, are included in the kits with buffers, such as Tris, phosphate, carbonate, etc., stabilizers, biocides, inert proteins, e.g., serum albumin, or the like. Frequently, it will be desirable to include an inert extender or excipient to dilute the active ingredients, where the excipient may be present in from about 1 to 99% of the total composition. Where antibodies capable of binding to the procollagen amino terminus and to the peptides of the invention are employed in an assay, they will typically be present in a separate vial.

Monoclonal antibodies for diagnostic uses, which bind the amino terminus of human procollagen Type I and peptides of the invention, can be produced by a variety of means. The production of murine monoclonal antibodies is well known and may be accomplished by, for example, immunizing the animal with a recombinant or synthetic peptide molecule or a selected portion thereof (e.g., an epitopic domain which competes with an epitope of the amino terminus of human procollagen Type I). Antibody producing cells obtained from the immunized animal are immortalized and screened, or screened first for, e.g., the production of antibody which functions in a competition assay using peptide and amino terminal procollagen molecules, and then immortalized. Antisera (polyclonal antibodies) or monospecific antibodies typically are non-human in origin, such as rabbit, goat, mouse, etc., and can be prepared by immunizing with appropriate peptides, which often will be conjugated to a carrier, e.g., keyhole limpet hemocyanin, for increased immunogenicity. The preparation of antibodies in this manner is well known in the art, such as described in Harlow and Lane, supra.

As mentioned above, various assay protocols may be employed for detecting the presence and/or levels of the amino-terminal propeptide of procollagen Type I in a sample. The peptide may be immobilized either directly or indirectly on a surface, where antibody to the peptide in the sample will become bound to the peptide on the surface. The presence of antibody bound to the peptide can then be detected by employing a xenogeneic antibody specific for the immunoglobulin, normally both IgG and IgM, or a labeled protein specific for immune complexes, e.g., Rf factor or *S. aureus* protein A or protein G.

The following examples are offered by way of illustration, not by way of limitation.

EXAMPLE I

RIA for Amino Terminal Type I Procollagen

The pro-α chains of type I collagen circulate in large quantities in human sera. Since these chains are a direct result of type I collagen synthesis, their measurement is used as a determinant of new bone production.

Antibodies were made to a synthetic peptide of the sequence Gln-Glu-Glu-Gly-Gln-Val-Glu-Gly-Gln-Asp-Glu-Asp-Tyr-Cys [Seq. ID No. 2]. To produce these antibodies, the peptide was conjugated to KLH using m-Maleimidobenzoyl-N-hydroxysuccinimide ester (MBS) as described in Harlow and Lane, supra. The peptide-KLH immunogen was injected into rabbits using standard antibody production protocols. New Zealand White rabbits were injected (Day 1) with 50 µg of conjugated peptide in complete Freund's adjuvant, subcutaneously. Day 21 the rabbits were given 150 µg conjugated peptide in alum by intradermal or intramuscular injection. On Day 49 (4 weeks later), the rabbits received a third injection, same as Day 21. Five weeks later (Day 84) the animal received injections as before. Test bleeds were performed 10 days after the third and subsequent boosts. Assays were performed with the serum from the 4th injection.

Monospecific polyclonal antibodies prepared from the sera of immunized animals were then used to produce a sensitive and specific RIA marker assay for collagen synthesis as determined by circulating Type I pro-α amino terminal procollagen found in serum. The antibodies, in borate buffer, pH 8.4, were used with either a standard (native Type I procollagen amino propeptide or synthetic peptide) or unknown, and tracer molecule (synthetic peptide iodinated with $^{125}$I by the chloramine-T method (Hunter and Greenwood, Nature 194:495–496 (1962)) in a total volume of 250 µl and allowed to come to equilibrium overnight at 4° C. Phase separation was accomplished by adding diluted preimmune rabbit serum (typically 100 µl of a dilution to achieve optimal precipitation of the immune sera, usually 1:20 or 1:30), diluted secondary antibody (goat anti-rabbit IgG, typically 400 µl diluted as with the preimmune sera) and 200 µl of 8% polyethylene glycol. The samples were thoroughly mixed and incubated for three hours at room temperature. Precipitates were collected by centrifugation and bound and total $^{125}$I-labeled peptide was determined in a gamma counter. This peptide was specific to the peptide fragment in that it did not recognize peptides to the carboxy terminal procollagen or the collagen proteins of other species (sera of rat or dogs were tested).

As shown in FIG. 1, the monospecific antibodies bound to the amino terminal propeptide of type I collagen and the synthetic peptide displaced in parallel to the native protein.

This amino terminal assay in preliminary studies correlated with skeletal alkaline phosphatase (r=0.086, p<0.001), an indicator of bone formation (Farley et al., *Clin. Chem.* 27:2002–2007 (1981). It did not correlate with tartrate resistant acid phosphatase (r=0.016, n.s.), a marker for bone resorption. Samples tested were previously collected serum samples from normal children (n=4), adults (n=26), and patients with osteoporosis (n=10), hypoparathyroidism (n=4), or Pagets disease of bone (n=11). These RIAs were performed as above.

EXAMPLE II

ELISA Assay for Amino Terminus of Procollagen

For this ELISA-type assay for circulating immunoterminus of procollagen α1 Type I, the peptide antigen Gln-Glu-Glu-Gly-Gln-Val-Glu-Gly-Gln-Asp-Glu-Asp-Tyr-Cys [Seq. ID No. 2] is bound to the bottom of wells of a 96 well plate. This is accomplished by first conjugating the peptide to a different carrier protein or by directly cross-linking the peptide to either an aminated or carboxylated plate (Costar). The test solution (either the titrated peptide, unknown serum sample, or control) is incubated together with the anti-peptide antibodies described in Example I. After a short incubation period, the mixture is placed in the wells containing the bound peptide, and any free (unbound) antibody is bound to the plate. After washing, the presence of bound antibodies is detected using a labeled secondary antibody, such as anti-rabbit IgG conjugated to HRP (horseradish peroxidase), then adding a color substrate, such as peroxidase substrate 2,2'-Azino-bis(3-Ethylbenzthiazoline-6-Sulfonic Acid) or ABTS. When high concentrations of amino terminal propeptides of α1 Type I collagen are present in the test solution, little antibody will bind to the place, thus the color reaction is low. When little or no antigen is present, the antibodies will bind completely to the antigen on the place, causing a high color state. To quantitate the levels of antigen, the peptide is titrated, making a standard curve to compare against the unknown sample.

A modification of this technique allows that the antibodies are first purified and conjugated to a label (such as HRP or alkaline phosphatase or biotin) directly, thus eliminating problems caused by the extra steps of the secondary reactions.

EXAMPLE III

Measurement of Bone Formation in Patients with Patients Disease

Figure 2:
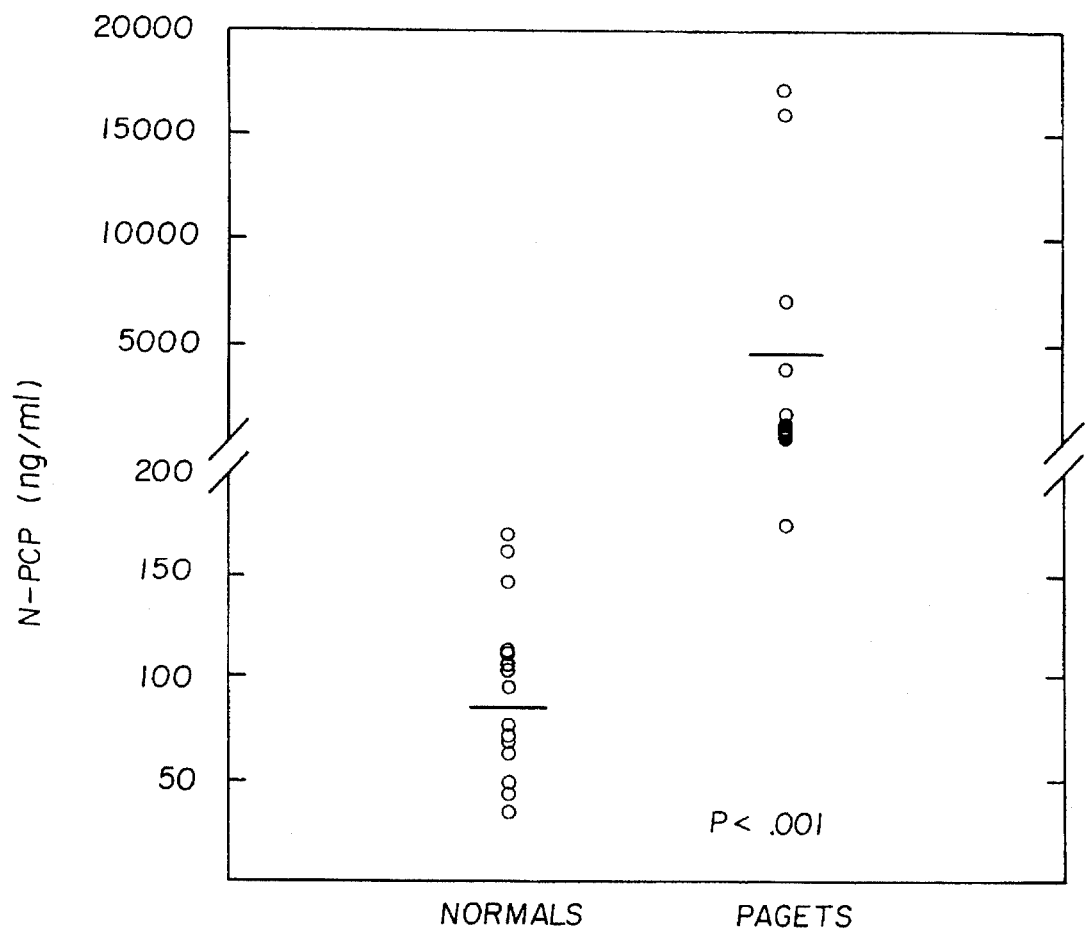
FIG. 2 is a graph of N-PCP concentration (ng/ml) versus normal patient (Normals) and patients with Paget's disease (Pagets), which shows a large difference in mean values between the two groups. A break appears in the scale for the y-axis.

The RIA described in Example I was used to determine differences in procollagen turnover, and hence bone formation, in patients with Paget's disease compared to healthy controls as described in Example I. The results showed a greater than 50-fold difference between serum levels of the amino terminus of procollagen of normals patients versus serum from the patients with Paget's disease of bone (see FIG. 2). These data support the conclusion that a synthetic peptide which mimics at least one selected epitope in the amino terminus of procollagen Type I, and antibody to the peptide have the ability to measure changes in bone formation rates independent of bone resorption.

Although the foregoing invention has been described in some detail by way of illustration and example for purposes of clarity of understanding, it will be apparent that certain changes and modifications may be practiced within the scope of the appended claims.

---

What is claimed is:

1. A synthetic or recombinantly produced polypeptide containing from six to fifty amino acids, wherein said polypeptide comprises from six to twelve contiguous amino acids contained in the sequence Gln-Glu-Glu-Gly-Gln-Val-Glu-Gly-Gln-Asp-Glu-Asp ($PEP_{23-34}$ (Seq. ID No. 1)), wherein said six to twelve contiguous amino acids are the only amino acids in said polypeptide that immunologically compete by specific binding with amino-terminal propeptide of procollagen α1 Type I.

2. The polypeptide of claim 1, further comprising at least one Cys or Tyr residue at the N- or C-terminus.

3. The polypeptide of claim 2, wherein the C-terminal residues comprise Tyr-Cys.

4. A synthetic or recombinantly produced polypeptide containing from six to fifty amino acids, wherein said polypeptide comprises from six to twelve contiguous amino acids contained in the sequence Val-Glu-Gly-Gln-Asp-Glu-Asp-Ile-Pro ($PEP_{28-36}$ (Seq. ID No. 3)), wherein said six to twelve amino acids are the only amino acids in said polypeptide that immunologically compete by specific binding with amino-terminal propeptide of procollagen α1 Type I.

5. The polypeptide of claim 4, further comprising at least one Cys or Tyr residue at the N- or C-terminus.

6. A method for determining the presence of amino terminal propeptide of procollagen Type I in an individual, comprising:

incubating under conditions conducive to immune complex formation (a) a sample from the individual, (b) a purified antibody which is immunologically reactive with an epitope contained within the sequence Gln-Glu-Glu-Gly-Gln-Val-Glu-Gly-Gln-Asp-Glu-Asp ($PEP_{23-34}$ (Seq. ID No. 1)) which epitope is immunologically competitive with an epitope of amino terminal propeptide of procollagen α1 Type I, and (c) a polypeptide which immunologically binds the antibody and which is labeled to provide a detectable signal, and detecting said label and therefrom determining the presence of the amino terminal propeptide of procollagen α1 Type I in said individual.

7. The method of claim 6, wherein the polypeptide is of the sequence ($PEP_{23-34}$ [Seq. ID No. 1]) X-Gln-Glu-Glu-Gly-Gln-Val-Glu-Gly-Gln-Asp-Glu-Asp-X wherein X is optionally present and comprises when present at least one Cys and or Tyr.

8. The method of claim 6, wherein the sample, antibody and polypeptide are incubated simultaneously.

9. The method of claim 6, wherein the incubation of the polypeptide with the sample and antibody is subsequent to a first incubation of the sample with the antibody.

10. The method of claim 9, wherein the incubation steps are separated by a wash step.

11. The method of claim 6, wherein the antibody is immobilized on a support.

12. The method of claim 11, wherein the support is insoluble.

13. The method of claim 6, wherein the polypeptide is labeled with an antibody which binds the polypeptide.

14. The method of claim 6, wherein the sample is human serum, plasma, urine, wound fluid or cell culture supernatant.

15. The method of claim 6, wherein the label is an enzyme, fluorescer, radionuclide, chemiluminescer or dye.

16. The method of claim 15, wherein the label is $^{125}I$ or $^{131}I$.

17. A method for determining the presence of amino terminal propeptide of procollagen Type I in an individual, comprising:

(a) incubating, under conditions conducive to the formation of immune complexes, a sample from the individual and a purified antibody, which is immunologically reactive with an epitope contained within the sequence Gln-Glu-Glu-Gly-Gln-Val-Glu-Gly-Gln-Asp-Glu-Asp (PEP$_{23-34}$ (Seq. ID No. 1)), which epitope is immunologically competitive with an epitope of amino terminal propeptide of procollagen α1 Type I;

(b) incubating, either simultaneously with or subsequently to the incubation of sample and antibody, a polypeptide bound to a carrier, which polypeptide immunologically binds to the antibody;

(c) separating the immune complexes bound to the carrier from unbound substances;

(d) incubating the separated immune complexes bound to the carrier with an antibody, which binds to amino terminal propeptide of procollagen α1 Type I;

(e) detecting the presence of immune complexes; and (f) determining therefrom the presence of the amino terminal propeptide of procollagen α1 type I in said individual.

18. A method for monitoring the rate of bone formation in a patient, which method comprises:

(a) incubating, under conditions conducive to formation of immune complexes, (i) a sample from the patient, (ii) a purified antibody, which is immunologically reactive with an epitope contained within the sequence Gln-Glu-Glu-Gly-Gln-Val-Glu-Gly-Gln-Asp-Glu-Asp (PEP$_{23-34}$; Seq. ID No. 1), which epitope is immunologically competitive with an epitope of amino terminal propeptide of procollagen α1 Type I, and (iii) a polypeptide, which immunologically binds the antibody and is labeled to provide a detectable signal;

(b) detecting said detectable signal; and (c) determining therefrom the presence and relative concentration of the amino terminal propeptide of procollagen α1 Type I in samples taken over a period of time from the patient, wherein an increase in the relative concentration of the amino-terminal propeptide of procollagen α1 Type I over time is indicative of a bone resorption disorder.

19. A test kit for determining the presence of amino terminal propeptide of procollagen Type I in an individual, which comprises:

a purified antibody which is immunologically reactive with an epitope contained within the sequence Gln-Glu-Glu-Gly-Gln-Val-Glu-Gly-Gln-Asp-Glu-Asp (PEP$_{23-34}$ (Seq. ID No. 1)) which epitope is immunologically competitive with an epitope of amino terminal propeptide of procollagen α1 Type I, and a labeled polypeptide which immunologically binds the antibody.

20. The kit of claim 19, wherein the polypeptide is of the sequence:

(PEP$_{23-34}$ (Seq. ID No. 1)) X-Gln-Glu-Glu-Gly-Gln-Val-Glu-Gly-Gln-Asp-Glu-Asp-Y, wherein each of X and Y is optionally present and comprises, when present, at least one Cys or Tyr.

21. The kit of claim 19, wherein the labeled polypeptide is labeled with a label selected from the group consisting of an enzyme, fluorescer, radionuclide, chemiluminescer, and dye.

22. The kit of claim 19, wherein the antibody comprises polyclonal antiserum obtained from an animal immunized with a synthetic peptide which contains an epitope within the sequence Gln-Glu-Glu-Gly-Gln-Val-Glu-Gly-Gln-Asp-Glu-Asp (PEP$_{23-34}$ which is immunologically competitive with an epitope of amino terminal propeptide of procollagen α1 Type I.

* * * * *

UNITED STATES PATENT AND TRADEMARK OFFICE
CERTIFICATE OF CORRECTION

PATENT NO. : 5,599,679
DATED : February 4, 1997
INVENTOR(S) : Baylink et al.

It is certified that error appears in the above-identified patent and that said Letters Patent is hereby corrected as shown below:

Column 4, line 41, replace "pro" with --Pro--.
Claim 17, line 11, replace "al" with --α1--.

Signed and Sealed this

Ninth Day of May, 2000

Attest:

Attesting Officer

Q. TODD DICKINSON

Director of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:

(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Gln Glu Glu Gly Gln Val Glu Gly Gln Asp Glu Asp
1               5                   10

(2) INFORMATION FOR SEQ ID NO:2:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

Gln Glu Glu Gly Gln Val Glu Gly Gln Asp Glu Asp Tyr Cys
1               5                   10

(2) INFORMATION FOR SEQ ID NO:3:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

Glu Gly Gln Asp Glu Asp Ile Pro
1               5

(2) INFORMATION FOR SEQ ID NO:4:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

Arg Tyr His Asp Arg Asp Val Trp
1               5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Val Trp Lys Pro Glu Pro Cys
1               5

(2) INFORMATION FOR SEQ ID NO:6:

(i) SEQUENCE CHARACTERISTICS:

( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Asp  Glu  Thr  Lys  Asn  Cys  Pro
      1                   5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Ala  Glu  Val  Pro  Glu  Gly  Glu  Cys
      1                   5

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Asp  Gly  Ser  Glu  Ser  Pro  Thr  Asp  Gln  Glu  Thr  Thr
      1                   5                        1 0

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Gly  Pro  Lys  Gly  Asp  Thr  Gly  Pro  Arg  Gly
      1                   5                        1 0

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Gly  Arg  Asp  Gly  Ile  Pro  Gly  Gln
      1                   5

( 2 ) INFORMATION FOR SEQ ID NO:11:

( i ) SEQUENCE CHARACTERISTICS:

(A) LENGTH: 160 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

| Met 1 | Phe | Ser | Phe | Val 5 | Asp | Leu | Arg | Leu | Leu 10 | Leu | Leu | Leu | Ala | Ala 15 | Thr |
|---|---|---|---|---|---|---|---|---|---|---|---|---|---|---|---|
| Ala | Leu | Leu | Thr 20 | His | Gly | Gln | Glu | Glu 25 | Gly | Gln | Val | Glu | Gly 30 | Gln | Asp |
| Glu | Asp | Ile 35 | Pro | Pro | Ile | Thr | Cys 40 | Val | Gln | Asn | Gly | Leu 45 | Arg | Tyr | His |
| Asp | Arg 50 | Asp | Val | Trp | Lys | Pro 55 | Glu | Pro | Cys | Arg | Ile 60 | Cys | Val | Cys | Asp |
| Asn 65 | Gly | Lys | Val | Leu | Cys 70 | Asp | Asp | Val | Ile | Cys 75 | Asp | Glu | Thr | Lys | Asn 80 |
| Cys | Pro | Gly | Ala | Glu 85 | Val | Pro | Glu | Gly | Glu 90 | Cys | Cys | Pro | Val | Cys 95 | Pro |
| Asp | Gly | Ser | Glu 100 | Ser | Pro | Thr | Asp | Gln 105 | Glu | Thr | Thr | Gly | Val 110 | Glu | Gly |
| Pro | Lys | Gly 115 | Asp | Thr | Gly | Pro | Arg 120 | Gly | Pro | Arg | Gly | Pro 125 | Ala | Gly | Pro |
| Pro | Gly 130 | Arg | Asp | Gly | Ile | Pro 135 | Gly | Gln | Pro | Gly | Leu 140 | Pro | Gly | Pro | Pro |
| Gly 145 | Pro | Pro | Gly | Pro | Pro 150 | Gly | Pro | Pro | Gly | Leu 155 | Gly | Gly | Asn | Phe | Ala 160 |